US010813915B2

(12) United States Patent
Cano et al.

(10) Patent No.: US 10,813,915 B2
(45) Date of Patent: Oct. 27, 2020

(54) PROMOTING SLEEP USING AT1 RECEPTOR BLOCKERS

(71) Applicant: University of Pittsburgh—of the Commonwealth System of Higher Education, Pittsburgh, PA (US)

(72) Inventors: Georgina Cano, Pittsburgh, PA (US); Alan F. Sved, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 590 days.

(21) Appl. No.: 14/340,505

(22) Filed: Jul. 24, 2014

(65) Prior Publication Data

US 2015/0150853 A1  Jun. 4, 2015

Related U.S. Application Data

(63) Continuation of application No. PCT/US2013/024844, filed on Feb. 6, 2013.

(60) Provisional application No. 61/595,974, filed on Feb. 7, 2012.

(51) Int. Cl.
| | | |
|---|---|---|
| A61K 36/38 | (2006.01) | |
| A61K 36/00 | (2006.01) | |
| A61K 31/4245 | (2006.01) | |
| A61K 45/06 | (2006.01) | |
| A61K 31/4184 | (2006.01) | |
| A61K 31/41 | (2006.01) | |
| A61K 31/4178 | (2006.01) | |

(52) U.S. Cl.
CPC .......... *A61K 31/4245* (2013.01); *A61K 31/41* (2013.01); *A61K 31/4178* (2013.01); *A61K 31/4184* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2003/0054041 A1* | 3/2003 | Lemmens | ............ | A61K 9/1652 424/489 |
| 2006/0159726 A1 | 7/2006 | Shell et al. | | |
| 2007/0060655 A1* | 3/2007 | Delalleau | ............ | A61K 31/165 514/630 |
| 2008/0167291 A1* | 7/2008 | Barlow | ................ | A61K 31/195 514/212.07 |

FOREIGN PATENT DOCUMENTS

| | | | |
|---|---|---|---|
| JP | 2005-162745 | | 6/2005 |
| WO | WO0178725 A2 | * | 10/2001 |
| WO | WO178725 A2 | * | 10/2001 |
| WO | WO2008122100 | * | 10/2008 |

OTHER PUBLICATIONS

Miura et al., "Do all angiotensin II type 1 receptor blockers have the same beneficial effects?", British Journal of Pharmacology, 151:912-913 (2007).
Miura et al., "Molecular mechanism underlying inverse agonist of angiotensin II type 1 receptor", The Journal of Biological Chemistry, 281(28):19288-19295 (Jul. 2006).
White et al., "Effects of the angiotensin receptor blocker azilsartan medoxomil versus olmesartan and valsartan on ambulatory and clinic blood pressure in patients with stages 1 and 2 hypertension", Hypertension, 57:413-420 (2011).
Imaizumi et al., "Class- and molecule-specific differential effects of angiotensin !! tyoe 1 receptor blockers", Curr. Pharm. Des., (Abstract only) (2012).
Mayorov et al., "Brain angiotensin AT1 receptors as specific regulators of cardiovascular reactivity to acute psychoemotional stress", clinical and Experimental Pharmacology and physiology, 38:126-135 (2011).
Neubauer, "New directions in the pharmacologic treatment of insomnia", Primary Psychiatry, 13(8):51-57 (2006).
Becker et al., "Effect of nasal continuous positive airway pressure treatment on blood pressure in patients with obstructive sleep apnea", Circulation, 107:68-73 (2003).
Samizo et al., "Comparison of losartan with ACE inhibitors and dihydropyridine calcium channel antagonists", Drug Safety, 25(11):811-821 (2002).
Vgontzas, et al., "Sleep and its disorders", Annu Rev Med., 50:387-400 (1999).
Nowell, et al., "Clinical factors contributing to the differential diagnosis of primary insomnia and insomnia related to mental disorders", Am J Psychiatry, 154:1412-1416 (1997).
Richardson, et al., "Future directions in the management of insomnia", J Clin Psychiatry, 62 (Suppl 10):39-45 (2001).
Rodenbeck, et al., "Interactions between evening and nocturnal cortisol secretion and sleep parameters in patients with severe chronic primary insomnia", Neurosci Lett., 324:159-163 (2002).
Sutton, et al., "Insomnia and health problems in Canadians", Sleep, 24:665-670 (2001).
Benca, "Sleep in psychiatric disorders", Neurol Clin., 14:739-764 (1996).

(Continued)

*Primary Examiner* — Michael Barker
*Assistant Examiner* — Randall Winston
(74) *Attorney, Agent, or Firm* — Baker Botts L.L.P.

(57) ABSTRACT

The present invention relates to the use of an Angiotensin II type 1 (AT1) receptor blocker for promoting sleep and/or the treatment of insomnia. It is based, at least in part, on the results of experiments performed using a validated rat model of stress-induced insomnia in which candesartan was found to ameliorate sleep disturbances induced by stress. Further, it was observed that this effect seems to be caused by blockade of AT1 receptors located in several brain regions that are key components of the neural circuitry activated during insomnia. In contrast to currently marketed treatments for insomnia, the AT1 receptor blocker was found to restore normal sleep without inhibiting REM sleep and/or inducing atypical wave components in the EEG.

16 Claims, No Drawings

(56) References Cited

OTHER PUBLICATIONS

Vgontzas, et al., "Chronic insomnia and activity of the stress system: a preliminary study", J Psychosom Res., 45:21-31 (1998).

Margolis, "Prevalence, costs, and consequences of insomnia. Reference bibliography: 1993-1998", Sleep, 22 (Suppl 2):S409-412 (1999).

Mignot, et al., "Sleeping with the hypothalamus: emerging therapeutic targets for sleep disorders", Nat Neurosci., 5 Suppl:1071-1075 (2002).

Kales, et al., "Rebound insomnia: a new clinical syndrome", Science, 201:1039-1041 (1978).

Walsh, "Pharmacologic management of insomnia", J Clin Psychiatry, 65 (Suppl 6):41-45 (2004).

Fleck, "Molecular actions of (S)-desmethylzopiclone (SEP-174559), an anxiolytic metabolite of zopiclone", J Pharmacol Exp Ther., 302:612-618 (2002).

Langer, et al., "Zolpidem and alpidem: two imidazopyridines with selectivity for omega 1- and omega 3-receptor subtypes", Adv Biochem Psychopharmacol., 46:61-72 (1990).

Rodenbeck, et al., "Neuroendocrine dysregulation in primary insomnia", Rev Neurol (Paris), 157:S57-61 (2001).

Davidson, et al., "Chronic stress, catecholamines, and sleep disturbance at Three Mile Island", J Human Stress, 13:75-83 (1987).

Saavedra, et al., "Brain angiotensin II: new developments, unanswered questions and therapeutic opportunities", Cell Mol Neurobiol., 25:485-512 (2005).

Saavedra, et al., "Brain and peripheral angiotensin II play a major role in stress", Stress, 10:185-193 (2007).

Saavedra, et al., "Anti-stress and anti-anxiety effects of centrally acting angiotensin II AT1 receptor antagonists", Regul Pept., 128:227-238 (2005).

Watanabe, et al., "Stress and brain angiotensin II receptors", Crit Rev Neurobiol., 12:305-317 (1998).

Grove, et al., "Angiotensin II receptors in the ventral portion of the bed nucleus of the stria terminalis", Neuroendocrinology, 53:339-343 (1991).

Lenkei, et al., "Expression of angiotensin type-1 (AT1) and type-2 (AT2) receptor mRNAs in the adult rat brain: a functional neuroanatomical review", Front Neuroendocrinol., 18:383-439 (1997).

Song, et al., "Mapping of angiotensin II receptor subtype heterogeneity in rat brain", J Comp Neurol., 316:467-484 (1992).

Cano, et al., "Neural circuitry of stress-induced insomnia in rats", J Neurosci., 28:10167-10184 (2008).

Nofzinger, et al., "Functional neuroimaging evidence for hyperarousal in insomnia", Am J Psychiatry, 161:2126-2128 (2004).

International Search Report and Written Opinion for PCT/US2013/024844, dated May 29, 2013.

\* cited by examiner

PROMOTING SLEEP USING AT1 RECEPTOR BLOCKERS

CROSS-REFERENCE TO RELATED APPLICATIONS

This application is a continuation of International Application Serial No. PCT/US13/024844, filed Feb. 6, 2013, which claims priority from U.S. Provisional Application Ser. No. 61/595,974, filed Feb. 7, 2012, each of which is hereby incorporated by reference in its entirety herein.

GRANT INFORMATION

This invention was made with government support under Grant No. RO3 MH097037 awarded by the National Institutes of Health/National Institute of Mental Health. The government has certain rights in the invention.

1. INTRODUCTION

The present invention relates to the use of Angiotensin II type I (AT1) receptor blockers for promoting sleep and/or the treatment of insomnia.

2. BACKGROUND OF THE INVENTION

2.1 Insomnia

Insomnia is the most prevalent sleep disorder, with an incidence ranging from 10-24% in the adult population of industrial countries (1-5). A much larger number of people suffer from occasional insomnia caused by stressful life events. Insomnia is also a cardinal feature of several psychiatric disorders such as depression, schizophrenia, anxiety, and post-traumatic stress disorder (6). Insomnia is associated with detrimental effects on general health and daily performance, including impaired memory, psychomotor deficits, daytime sleepiness, physical and mental fatigue, anxiety and irritability (1, 3, 8). Most importantly, insomnia is a critical risk factor for developing psychiatric disorders, especially depression. Current treatments for insomnia are unspecific and target the symptoms instead of the pathologic alterations underling those symptoms (9), causing undesirable side effects as well as high risk for abuse and dependence. Therefore, the development of improved and more specific pharmacotherapy for the treatment of insomnia is a top priority.

Insomnia is triggered by stressful life events in predisposed individuals. In general, the stress system seems to be hyperactive in insomniacs, as demonstrated by increased neuroendocrine and sympathoadrenal system (SAS) activity (19). Increased nocturnal plasma and urinary cortisol levels correlate with impaired sleep parameters (nocturnal awakenings; 4,7,14). SAS activation has been reported in chronic insomniacs, and chronically stressed subjects who experience sleep disturbances have elevated levels of urinary and circulating catecholamines (7,15), increased basal metabolism, body temperature, heart rate, peripheral vasoconstriction, body movement, muscle tension and altered pupillometry patterns (1,3). These physiological changes are similar to those observed during stress-evoked sympathetic responses. A key mediator of the stress response is corticotropin releasing hormone (CRH), a neuropeptide that has a dual central action as the initiator of the HPA axis cascade and as an activator of the SAS response. CRH hyperactivity can produce both the sleep disturbances and the physiological arousal characteristic of insomnia (3). Richardson and Roth (3) have proposed that increased activity of CRH neurons, especially those innervating the locus coeruleus (LC), may play a role in the pathogenesis of insomnia.

A rat model of stress-induced insomnia has been developed using a psychosocial stressor. This model has enabled the characterization of the neuroanatomical circuitry that becomes activated (24). It was found that there is simultaneous activation of the sleep-promoting areas, driven by the circadian and homeostatic drives, and the limbic and arousal systems activated by emotional stress. By placing selective brain lesions, the sequence of events was determined: the limbic system becomes activated first and, in turn, activates part of the arousal system, which subsequently activates the cerebral cortex, causing the sleep disturbances observed in insomnia. PET studies in humans with primary insomnia have shown increased activity in these same brain regions during impaired sleep (25), suggesting that a similar neuroanatomic circuitry is activated in the rat model and in humans with insomnia. Two relevant limbic structures that are key initiators of the cascade of events occurring in insomnia in the model, the bed nucleus of the stria terminalis and the central nucleus of the amygdala, express Angiotensin II type 1 (AT1) receptors.

2.2 Angiotensin II and Stress

Peripheral Angiotensin II (Ang II) is well known for its role in cardiovascular regulation, but central (brain) Ang II plays an important role in stress responses (16-19). Central Ang II and AT1 receptor expression increase during stress responses and, in turn, activate both the neuroendocrine and sympathoadrenal systems. These effects can be blocked by administration of Ang II antagonists or mimicked by central Ang II administration (18-10). AT1 receptors have been identified in regions involved in stress responses (21-23), suggesting that this effect of Ang II occurs via direct activation of these neurons. Emerging evidence suggest that brain AT1 receptors are primarily involved in the regulation of cardiovascular arousal during stress responses, mainly during psycho-emotional stress.

2.3 Anti-Insomnia Medications

The currently available drugs for treating insomnia fall into mainly four classes. One group includes the antihistaminergic drugs, which block the H1 receptor for histamine. These drugs are not very potent and, more importantly, do not produce reliable sleep in many people with insomnia.

The second class of drugs for insomnia comprises drugs that enhance inhibitory neurotransmission in the entire brain by activating GABA-A receptors, which are located virtually in all brain neurons. This class includes benzodiazepines (BZ) and non-BZ compounds that act on the BZ site of GABA A receptors (also known as Z-drugs). BZ are widely used because of their margin of safety, but they often cause undesirable side effects such as daytime drowsiness and impairment of motor coordination, memory and cognitive performance, as well as exacerbation of breathing disorders during sleep. In addition, BZ use is associated with high risk for abuse, dependence, withdrawal, and rebound insomnia (1, 10). More recently, Z-drugs such as zolpidem (Ambien), zaleplon (Sonata), and eszopiclone (Lunesta) have been marketed to treat insomnia, but these drugs still cause unwanted side-effects, mainly daytime sedation and impairment of locomotor coordination (12,13). In general, BZ and Z-drugs do not restore normal sleep as all these drugs decrease REM sleep substantially (and nREM stage 4 or deep sleep in some cases) and some of them also induce a sigma component in the EEG that is not typical of normal sleep. The function of REM sleep is still a controversial topic, but numerous studies support an important role in learning and memory consolidation. Indeed, the cognitive impairment commonly associated to BZ and Z-drugs treatments may be due in part to decreased REM sleep. Therefore, restoration of normal REM sleep should be considered in any putative pharmacologic treatment for insomnia.

The third class of drugs includes the agonists for the melatonin receptors. Melatonin is responsible for maintaining the 24 hour circadian cycle which regulates many different body functions. Melatonin (MT1 and MT2) agonists are used to treat mainly primary "sleep-onset" insomnia and jetlag, as well as circadian sleep disorders. They are effective in reducing sleep onset (time to fall asleep) and reset the circadian rhythm, and they have limited adverse effects. However, they are less effective in improving sleep maintenance and are not effective in most cases of insomnia.

Lastly, the use of antidepressants for the treatment of insomnia has been increasing dramatically, becoming the second most prescribed drug for insomnia in the USA. Because BZ treatment is not recommended for long term use and because insomnia is highly correlated with depression, antidepressants are frequently prescribed to treat insomnia despite inadequate data to support their efficacy (11) and a potential for serious side effects. Antidepressants are known to drastically suppress REM sleep, which might be related to the memory impairment commonly associated to these drugs.

Cognitive behavioral therapy for insomnia provides symptomatic relief and improved sleep; however, the number of patients that would benefit from this approach greatly exceeds the available resources. Hence, pharmacologic therapies constitute the most realistic treatment for the large number of individuals experiencing insomnia.

3. SUMMARY OF THE INVENTION

The present invention relates to the use of an Angiotensin II type 1 (AT1) receptor blocker for promoting sleep and/or the treatment of insomnia. It is based, at least in part, on the results of experiments performed in a validated rat model of stress-induced insomnia in which candesartan, an AT1 receptor blocker with antagonist action, or azilsartan, an AT1 receptor blocker with inverse agonist action, were found to ameliorate sleep disturbances induced by stress. Further, it was observed that this effect seems to be caused by blockade of AT1 receptors located in several brain regions that are key components of the neural circuitry activated during insomnia. In contrast to currently marketed treatments for insomnia, the AT1 receptor blockers were found to restore normal sleep without inhibiting REM sleep and/or inducing atypical wave components in the EEG.

Advantages of AT1 receptor blockers as treatments for insomnia include the following:
1) decreased sleep latency (difficulties falling asleep);
2) increased nREM sleep;
3) less or no suppression of REM sleep;
4) less or no abnormal wave components (sigma waves) in the EEG;
5 greater specificity than BZ and Z-drugs because their effects are mediated by inhibition of brain areas that are part of the neural circuitry activated by insomnia rather than the whole entire brain;
6) because of their higher specificity, these drugs would be expected to have fewer side effects; and
7) these drugs are in a class already approved by the FDA which have been found to be safe and well tolerated.

4. DETAILED DESCRIPTION OF THE INVENTION

For clarity of disclosure, and not by way of limitation, this detailed description is divided into the following subsections:
(i) AT1 receptor blockers;
(ii) combinations of AT1 receptor blockers with other agents; and
(iii) methods of treatment.

4.1 AT1 Receptor Blockers

An AT1 receptor blocker is an agent that binds to the AT1 receptor under physiological conditions and inhibits the effect of angiotensin II on the AT1 receptor (is an AT1 receptor antagonist) and/or is an agent that binds to the AT1 receptor and, when bound to the receptor, results in an effect opposite to the effect produced when angiotensin II binds to the receptor (is an inverse agonist of the AT1 receptor). See, for example, refs. 26-28. It is understood that an agent can potentially exhibit both antagonist and inverse agonist activity. Non-limiting examples of AT1 receptor blockers include azilsartan (Edarbi®), candesartan (Atacand®), eprosartan (Teveten®), irbesartan (Aprovel®), losartan (Cozaar®), olmesartan (Olmetec®), telmisartan (Micardis®), valsartan (Diovan®) and EXP 3174. In certain non-limiting embodiments, the AT1 receptor blocker exhibits substantial inverse agonist activity in vitro and/or in vivo (for example, ranging from significant detectable inverse agonist activity to where inverse agonist activity is the predominant or is the only detectable mode of action); examples of such agents include but are not limited to azilsartan, candesartan and olmesartan In non-limiting embodiments, the present invention provides for a pharmaceutical composition comprising a unit dose of AT1 receptor blocker that is lower than the dosage used to treat hypertension, for example, a non-zero dose effective at treating insomnia which is at least 10% lower or at least 20% lower or at least 30% lower or at least 40% lower or at least 50% lower, than the dose used to treat hypertension. For example, and not by way of limitation, a pharmaceutical composition may comprise a unit dose of azilsartan which is at least 1 mg or at least 2 mg or at least 3 mg or at least 4 mg or at least 5 mg or at least 10 mg, up to 35 mg or up to 30 mg or up to 25 mg or up to 20 mg, or 1 mg, or 2 mg, or 3 mg, or 4 mg or 5 mg or 6 mg or 7 mg or 8 mg or 9 mg or 10 mg, or between about 1 and 5 mg or between about 2 and 5 mg or between about 2 and 7 mg or between about 3 and 8 mg or between about 1 and 10 mg or between about 5-10 mg, or between about 5-15 mg, or between about 10-20 mg, or between about 10-30 mg. For example, and not by way of limitation, a pharmaceutical composition may comprise a unit dose of candesartan which is at least 2.5 mg or at least 5 mg, up to 14 mg or up to 12 mg or up to 10 mg or up to 7 mg, or between about 2.5-7 mg, or between about 5-10 mg. For example, and not by way of limitation, a pharmaceutical composition may comprise a unit dose of eprosartan which is at least 50 mg or at least 100 mg, up to 350 mg or up to 300 mg or up to 250 mg or up to 200 mg, or between about 50-200 mg, or between about 100-300 mg. For example, and not by way of limitation, a pharmaceutical composition may comprise a unit dose of losartan which is at least 5 mg or at least 15 mg, up to 45 mg or up to 35 mg or up to 30 mg or up to 24 mg, or between about 5-20 mg, or between about 15-35 mg. For example, and not by way of limitation, a pharmaceutical composition may comprise a unit dose of olmesartan which is at least 5 mg or at least 10 mg, up to 35 mg or up to 30 mg or up to 25 mg or up to 20 mg or up to 15 mg, or between about 5-10 mg, or between about 5-15 mg, or between about 10-20 mg, or between about 10-30 mg. For example, and not by way of limitation, a pharmaceutical composition may comprise a unit dose of telmisartan which is at least 5 mg or at least 10 mg, up to 35 mg or up to 30 mg or up to 25 mg or up to 20 mg or up to 15 mg, or between about 5-10 mg, or between about 5-15 mg, or between about 10-20 mg, or between about 10-30 mg. For example, and not by way of limitation, a pharmaceutical composition may comprise a unit dose of valsartan which is at least 10 mg or at least 20 mg, up to 150 mg or up to 125 mg or up to 100 mg or up to 80 mg or up to 30 mg, or between about 10-80 mg, or between about 20-125 mg, or between about 40-80 mg, or between about 10-30 mg.

The present invention further provides for a pharmaceutical composition comprising an AT1 receptor blocker in a suitable pharmaceutical carrier, including, but nor limited to liquid carriers such as but not limited to water or saline or solid carriers including but not limited to tableting excipients such as one or more of starch, microcrystalline cellulose, hydroxypropylmethyl cellulose, dextrose, sucrose, mannitol, lactose, starch, polyvinylpyrrolidone, crospovidone, etc. Optionally such pharmaceutical composition may further comprise a homeopathic sleep aid such as but not limited to one or more of tryptophan, L-tryptophan, lavender, chamomile, valerian root, passionflower, lemon balm, inositol, magnesium, humulus lupus, hops extract, St. John's wort, or melatonin.

4.2 Combinations of AT1 Receptor Blockers with Other Agents

The present invention further provides for pharmaceutical compositions comprising an AT1 receptor blocker with another sleep promoting agent. A compound other than an AT1 receptor blocker which is used to promote sleep (not including homeopathic sleep aids tryptophan, L-tryptophan, lavender, chamomile, valerian root, passionflower, lemon balm, inositol, magnesium, humulus lupus, hops extract, St. John's wort, or melatonin) is referred to herein as "another sleep promoting agent" or a "second sleep promoting agent" or a "SSPA".

In one set of non-limiting embodiments, the present invention provides for a pharmaceutical composition comprising an AT1 receptor blocker together with a histamine type 1 receptor (H1) antagonist such as, but not limited to, diphenhydramine hydrochloride, doxepin, doxylamine succinate, orphenadrine, bromdiphenhydramine, or dimenhydrinate], in amounts that together are effective in treating insomnia.

In another set of non-limiting embodiments, the present invention provides for a pharmaceutical composition comprising an AT1 receptor blocker together with a histamine type 3 receptor (H3) agonist (such as Immepip, Imetit, Methimepip, Immethridine, R-alpha-methylhistamine, and 4-benzyl-1H-imidazole-based H3 receptor agonists) or an H3B agonist in amounts that together are effective in treating insomnia.

In another set of non-limiting embodiments, the present invention provides for a pharmaceutical composition comprising an AT1 receptor blocker together with a selective GABA A ligand with agonist activity at the alpha-3 or alpha-2/alpha-3 subunits in amounts that together are effective in treating insomnia.

In another set of non-limiting embodiments, the present invention provides for a pharmaceutical composition comprising an AT1 receptor blocker together with a SSPA selected from the group consisting of zolpidem (Ambien®), zaleplon (Sonata®) and eszopiclone (Lunesta®), in amounts that together are effective in treating insomnia.

In another set of non-limiting embodiments, the present invention provides for a pharmaceutical composition comprising an AT1 receptor blocker together with a benzodiazepine (such as diazepam (Valium®), clonazepam (Klonapin), lorazepam (Ativan®), or alprazolam (Xanax®)) in amounts that together are effective in treating insomnia.

In another set of non-limiting embodiments, the present invention provides for a pharmaceutical composition comprising an AT1 receptor blocker together with a corticotropin releasing hormone (CRH) antagonist in amounts that together are effective in treating insomnia.

In another set of non-limiting embodiments, the present invention provides for a pharmaceutical composition comprising an AT1 receptor blocker together with a melatonin receptor agonistacting on type 1 (MT1) and/or type 2 (MT2) receptors, such as Ramelteon, Agomelatine, Tasimelteon, TIK-301 or Circadin, in amounts that together are effective in treating insomnia.

The pharmaceutical composition comprising an AT1 receptor blocker and one or more other SSPA may further comprise a suitable pharmaceutical carrier, including, but nor limited to liquid carriers such as but not limited to water or saline or solid carriers including but not limited to tableting excipients such as one or more of starch, microcrystalline cellulose, hydroxypropylmethyl cellulose, dextrose, sucrose, mannitol, lactose, starch, polyvinylpyrrolidone, crospovidone, etc. Optionally such pharmaceutical composition may further comprise a homeopathic sleep aid such as but not limited to one or more of tryptophan, L-tryptophan, lavender, chamomile, valerian root, passionflower, lemon balm, inositol, magnesium, humulus lupus, hops extract, St. John's wort, or melatonin.

4.3 Methods of Treatment

The present invention provides for methods of promoting sleep in a subject in need of such treatment comprising administering, to the subject, a therapeutically effective amount of an AT1 receptor blocker. Such method may further comprise administering a homeopathic sleep aid and/or another sleep promoting agent (an SSPA, as defined above).

The present invention further provides for methods of treating insomnia comprising administering, to a subject in need of such treatment, a therapeutically effective amount of an AT1 receptor blocker. Such method may further comprise administering a homeopathic sleep aid and/or another sleep promoting agent (an SSPA, as defined above).

"Promoting sleep" means inducing falling asleep (e.g., decreased sleep latency) and/or promoting duration of sleep.

The methods of the invention may be used for the treatment of primary insomnia or secondary insomnia (co-morbid with depression or other psychiatric disorders).

"Insomnia" means difficulty sleeping, including difficulty falling asleep (increased sleep latency) and/or difficulty staying asleep (frequent awakenings or sleep fragmentation).

"Treating" or "treat" means one or more of the following: decreasing sleep latency (time elapsed between attempting to sleep and falling asleep); increasing nREM sleep; not suppressing REM sleep; and/or not inducing abnormal wave components (sigma waves) in the EEG.

The AT1 receptor blocker (and optionally homeopathic sleep aid or SSPA) may be administered by any route of administration including but not limited to oral, nasal, pulmonary, transdermal, rectal, subcutaneous, or intravenous.

In certain non-limiting embodiments of the invention, the AT1 receptor blocker (and optionally homeopathic sleep aid or SSPA) may be administered within 2 hours of the desired time of sleep onset.

In certain non-limiting embodiments, the inventive method may be used to promote sleep in an individual whose circadian rhythm has been disrupted for example by travel to another time zone or intention change in sleep habits.

The subject may be a human or non-human subject, for example a non-human primate, a dog, a cat, a horse, a rodent, etc.

The AT1 receptor blocker may be used at the typical clinical dosage used to treat hypertension or at a dosage lower than that used to treat hypertension, for example, a non-zero dose effective at treating insomnia which is at least 10% lower or at least 20% lower or at least 30% lower or at least 40% lower or at least 50% lower, than the dose used to treat hypertension. Exemplary human doses follow. For example, and not by way of limitation, azilsartan may be used at about 40 mg daily (a typical dose used to treat hypertension) or a dose of at least 1 mg or at least 2 mg or at least 3 mg or at least 4 mg or at least 5 mg or at least 10 mg, up to 35 mg or up to 30 mg or up to 25 mg or up to 20 mg, or between about 1 and 5 mg or between about 2 and 5 mg or between about 2 and 7 mg or between about 3 and 8 mg or between about 1 and 10 mg or between about 5-10 mg, or between about 5-15 mg, or between about 10-20 mg, or between about 10-30 mg daily. For example, and not by way of limitation, candesartan may be used at about 16 mg daily (a typical dose used to treat hypertension) or a dose of at least 2.5 mg or at least 5 mg, up to 14 mg or up to 12 mg or up to 10 mg or up to 8 mg, or between about 2.5-8 mg, or between about 5-10 mg daily. For example, and not by way of limitation, eprosartan may be used at about 400 mg daily (a typical dose used to treat hypertension) or a dose of at least 50 mg or at least 100 mg, up to 350 mg or up to 300 mg or up to 250 mg or up to 200 mg, or between about 50-200 mg, or between about 100-300 mg daily. For example, and not by way of limitation, losartan may be used at about 50 mg daily (a typical dose used to treat hypertension) or a dose of at least 5 mg or at least 15 mg, up to 45 mg or up to 35 mg or up to 30 mg or up to 25 mg, or between about 5-25 mg, or between about 15-35 mg daily. For example, and not by way of limitation, olmesartan may be used at about 40 mg daily (a typical dose used to treat hypertension) or a dose of at least 5 mg or at least 10 mg, up to 35 mg or up to 30 mg or up to 25 mg or up to 20 mg, or between about 5-10 mg, or between about 5-15 mg, or between about 10-20 mg, or between about 10-30 mg daily. For example, and not by way of limitation, telmisartan may be used at about 40 mg daily (a typical dose used to treat hypertension) or a dose of at least 5 mg or at least 10 mg, up to 35 mg or up to 30 mg or up to 25 mg or up to 20 mg, or between about 5-10 mg, or between about 5-15 mg, or between about 10-20 mg, or between about 10-30 mg daily. For example, and not by way of limitation, valsartan may be used at about 160 mg daily (a typical dose used to treat hypertension) or a dose of at least 10 mg or at least 20 mg, up to 150 mg or up to 125 mg or up to 100 mg or up to 80 mg, or between about 10-80 mg, or between about 20-125 mg, or between about 40-80 mg, or between about 10-30 mg daily.

The present invention further provides for the use of AT1 receptor blockers with SSPAs, as defined above. The AT1 receptor blocker and the SSPA may be comprised in the same or separate pharmaceutical formulations and may be administered together simultaneously or at different times provided that if they are not administered at the same time the second agent is administered such that both agents will be concurrently present in the patient at levels which in combination are effective in treating insomnia. The AT1 receptor blocker may be used at a dose set forth above. The SSPA may be used at a non-zero dose effective at treating insomnia in combination with the AT1 receptor blocker, where said non-zero dose of SSPA is lower (for example at least 10% lower or at least 20% lower or at least 30% lower or at least 40% lower or at least 50% lower) than the dose used to treat insomnia when the SSPA is used as the sole therapeutic agent.

In one set of non-limiting embodiments, the present invention provides for the use of an AT1 receptor blocker together with a H1 antagonist such as, but not limited to, diphenhydramine hydrochloride, doxepin, doxylamine succinate, orphenadrine, bromdiphenhydramine, or dimenhydrinate to treat insomnia, preferably where the H1 antagonist, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the H1 antagonist is used as the sole therapeutic agent.

In another set of non-limiting embodiments, the present invention provides for the use of an AT1 receptor blocker together with a H3 agonist (such as Immepip, Imetit, Methimepip, Immethridine, R-alpha-methylhistamine, and 4-benzyl-1H-imidazole-based H3 receptor agonists) or an H3B agonist to treat insomnia, preferably where the H3 or H3B agonist, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the H3 or H3B agonist is used as the sole therapeutic agent.

In another set of non-limiting embodiments, the present invention provides for the use of an AT1 receptor blocker together with a selective GABA A ligand with agonist activity at the alpha-3 or alpha-2/alpha-3 subunits to treat insomnia, preferably where the GABA A ligand, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the GABA A ligand is used as the sole therapeutic agent.

In another set of non-limiting embodiments, the present invention provides for the use of an AT1 receptor blocker together with a SSPA selected from the group consisting of zolpidem (Ambien®), zaleplon (Sonata®) and eszopiclone (Lunesta®), to treat insomnia, preferably where the sleep-promoting drug, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the SSPA is used as the sole therapeutic agent.

In another set of non-limiting embodiments, the present invention provides for the use of an AT1 receptor blocker together with a benzodiazepine (such as diazepam (Valium®), clonazepam (Klonapin), lorazepam (Ativan®), or alprazolam (Xanax®)) to treat insomnia, preferably where the benzodiazepine, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the benzodiazepine is used as the sole therapeutic agent.

In another set of non-limiting embodiments, the present invention provides for the use of an AT1 receptor blocker together with a corticotropin releasing hormone (CRH) antagonist that can cross the blood brain barrier to treat insomnia, preferably where the CRH antagonist, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the CRH antagonist is used as the sole therapeutic agent.

In another set of non-limiting embodiments, the present invention provides for the use of an AT1 receptor blocker together with a melatonin receptor agonist acting on MT1 and/or MT2 receptors, such as Ramelteon, Agomelatine, Tasimelteon, TIK-301 or Circadin, to treat insomnia, preferably where the melatonin receptor agonist, in combination with AT1 receptor blocker, is used at a therapeutically effective dose that is lower (for example at least 10% lower or at least 20% lower or at least 30% lower or at least 40% lower or at least 50% lower) than the dose used to treat insomnia when the melatonin receptor agonist is used as the sole therapeutic agent.

5. EXAMPLE 1

Rats in the stress-induced insomnia model (25) were treated with candesartan intraperitoneally (i.p.; 1 mg/kg or 5 mg/kg). In the model, insomnia is induced by transferring male rats at the peak of their normal sleep cycle into a soiled cage previously occupied during one week by another male rat. This simple procedure induces a psychological or social stress response in the rats, which are very territorial animals. The sequence of sleep disturbances in cage exchanged rats is similar to that observed in humans with primary insomnia. In rats, there is an initial delay in sleep onset and increased wakefulness that resemble the difficulties falling asleep at the beginning of the night, or initial insomnia, observed in humans after a stressful day. Eventually, insomniacs fall asleep because of the sleep pressure, as rats do. But later, as the night progresses, they usually experience insomnia characterized by decreased nREM sleep, frequent awakenings, and poor quality sleep, similar to what we observed in the stressed rats.

Candesartan was injected i.p. just prior to transferring the rats (n=7 for the 1 mg/kg treatment and n=4 for the 5 mg/kg treatment) to the soiled cage. EEG and EMG activity were recorded continuously to determine the behavioral state (wake, nREM or REM sleep) along several hours. Control rats (n=6) were injected with vehicle and also placed in a soiled cage and recorded. We found out that Candesartan treatment produces several effects:

Decreases the sleep latency from 68±10 minutes (vehicle) to 38±3 minutes (candesartan), therefore, drastically reduces the difficulties falling asleep characteristic of initial insomnia induced by stress.

Increases nREM sleep to levels similar to those before stress exposure. nREM sleep is increased 20-40% (depending on the hour) compared with vehicle treated rats.

Partially restores REM sleep, which is dramatically suppressed in the insomnia model. REM sleep is increased to 6-12% (depending on the hour) compared with vehicle treated rats (0-4%).

Both doses of candesartan (1 and 5 mg/kg) produced similar effects (with no significant differences), suggesting that the lower dose is effective to restore normal sleep (i.e., decreased latency and restored nREM and REM sleep) and, therefore, would likely cause less side effects.

Candesartan treatment does not induce abnormal wave components in the EEG, as observed in the power spectrum analysis.

Brains from treated rats show less activity in the limbic areas as well as inhibition of the arousal regions and the cortex, strongly suggesting that Candesartan specifically acts on brain regions that are part of the circuitry activated during insomnia.

Although the effects of stress are highly variable among rats, the effects of Candesartan on ameliorating sleep parameters seem to be remarkably consistent (very low variability) after 2 hours post-injection during the next 4 hours. We believe that the variability in the first 2 hours might be due to the delay of the drug in crossing the blood-brain barrier and reaching the brain after i.p. injection.

6. EXAMPLE 2

In an additional study, Azilsartan was tested using the same stress-induced insomnia model in rats as was used in Example 1. Azilsartan, which mainly acts as an inverse agonist of AT1 receptors, has been reported to have a potent effect in the treatment of hypertension at a single daily dose compared to twice-a-day doses commonly used for other AT1 receptor blockers. For this reason, we used a lower dose of azilsartan (0.5 mg/kg) than the dose used for candesartan. Azilsartan was injected i.p. just prior to transferring the rats (n=4) to the soiled cage. EEG and EMG activity were recorded continuously to determine the behavioral state (wake, nREM or REM sleep) along several hours, as explained above.

We found out that Azilsartan treatment at this low dose improves sleep in the animal insomnia model better than candesartan at higher doses:

The average of wakefulness along the entire experiment (aprox. 6 hours) after cage exchange and drug injection was decreased from 52% in vehicle-treated rats to 35% in candesartan-treated rats and 22% in azilsartan-treated rats. Conversely, the average of nREM sleep was increased from 45% in vehicle-treated rats to 57% and 68% in candesartan and azilsartan-treated rats, respectively, in the same time period. The percentage of nREM sleep in azilsartan-treated rats ranged from 50-82% depending on the hour. In addition, the average of REM sleep was increased from 2% in vehicle-treated rats to 7.5% in candesartan-treated rats and 10% in azilsartan-treated rats (ranging from 3-15% depending on the hour).

The effect of azilsartan seems to last longer, as rats showed 20% more sleep in the last two hours of the experiment (4 hours after injection of the drug) compared to candesartan-treated rats. Similarly, in humans treated for hypertension, azilsartan shows a longer-lasting effect than other AT1 receptor blockers.

Azilsartan treatment, as candesartan, does not seem to induce abnormal wave components in the EEG.

The sleep latency in azilsartan-treated rats was 60±3 minutes, which is just slightly reduced compared to non-treated rats (68±10 minutes) and does not reach the decreased sleep latency observed in candesartan-treated rats (38±3 minutes). Without being bound to any particular theory, this lack of decreased sleep latency (in contrast with the stronger effects in all other sleep parameters analyzed) could be due to the vehicle used to dissolve azilsartan (0.5% methyl cellulose), which has a viscosity of 15 cP. A drug dissolved in this viscous vehicle and injected intraperitoneally would have more difficulty to diffuse in the abdominal cavity and reach the blood brain barrier and pass into the brain. In contrast, candesartan was dissolved in a vehicle of low viscosity and therefore could have reached the brain much faster. Due to the characteristics of the vehicle used to dissolve azilsartan, it is difficult to assess the real sleep latency induced by this drug.

The results from rats subjected to the stress-induced insomnia model strongly support that AT1 receptor blockers can restore normal sleep in insomnia. AT1 receptor blockers that have a long-lasting effect, such as azilsartan, might be potentially useful for sleep maintenance (i.e. awakenings in the middle of the night) and/or early morning awakening, which are also common features of insomnia in humans. The sleep normalization effect obtained at such lower doses suggests that these drugs would potentially cause less undesirable side effects.

7. REFERENCES

1. Vgontzas, A. N. & Kales, A. Sleep and its disorders. Annu Rev Med 50, 387-400 (1999).
2. Nowell, P. D., et al. Clinical factors contributing to the differential diagnosis of primary insomnia and insomnia related to mental disorders. Am J Psychiatry 154, 1412-1416 (1997).
3. Richardson, G. S. & Roth, T. Future directions in the management of insomnia. J Clin Psychiatry 62 Suppl 10, 39-45 (2001).
4. Rodenbeck, A., Huether, G., Ruther, E. & Hajak, G. Interactions between evening and nocturnal cortisol secretion and sleep parameters in patients with severe chronic primary insomnia. Neurosci Lett 324, 159-163 (2002).
5. Sutton, D. A., Moldofsky, H. & Badley, E. M. Insomnia and health problems in Canadians. Sleep 24, 665-670 (2001).
6. Benca, R. M. Sleep in psychiatric disorders. Neurol Clin 14, 739-764 (1996).
7. Vgontzas, A. N., et al. Chronic insomnia and activity of the stress system: a preliminary study. J Psychosom Res 45, 21-31 (1998).
8. Margolis, N. Prevalence, costs, and consequences of insomnia. Reference bibliography: 1993-1998. Sleep 22 Suppl 2, S409-412 (1999).
9. Mignot, E., Taheri, S. & Nishino, S. Sleeping with the hypothalamus: emerging therapeutic targets for sleep disorders. Nat Neurosci 5 Suppl, 1071-1075 (2002).
10. Kales, A., Scharf, M. B. & Kales, J. D. Rebound insomnia: a new clinical syndrome. Science 201, 1039-1041 (1978).
11. Walsh, J. K. Pharmacologic management of insomnia. J Clin Psychiatry 65 Suppl 16, 41-45 (2004).
12. Fleck, M. W. Molecular actions of (S)-desmethylzopiclone (SEP-174559), an anxiolytic metabolite of zopiclone. J Pharmacol Exp Ther 302, 612-618 (2002).
13. Langer, S. Z., Arbilla, S., Benavides, J. & Scatton, B. Zolpidem and alpidem: two imidazopyridines with selectivity for omega 1- and omega 3-receptor subtypes. Adv Biochem Psychopharmacol 46, 61-72 (1990).
14. Rodenbeck, A. & Hajak, G. Neuroendocrine dysregulation in primary insomnia. Rev Neurol (Paris) 157, S57-61 (2001).
15. Davidson, L. M., Fleming, R. & Baum, A. Chronic stress, catecholamines, and sleep disturbance at Three Mile Island. J Human Stress 13, 75-83 (1987).
16. Mayorov, D. N. Brain angiotensin AT1 receptors as specific regulators of cardiovascular reactivity to acute psychoemotional stress. Clin Exp Pharmacol Physiol 38, 126-135 (2011).
17. Saavedra, J. M. Brain angiotensin II: new developments, unanswered questions and therapeutic opportunities. Cell Mol Neurobiol 25, 485-512 (2005).
18. Saavedra, J. M. & Benicky, J. Brain and peripheral angiotensin II play a major role in stress. Stress 10, 185-193 (2007).
19. Saavedra, J. M., et al. Anti-stress and anti-anxiety effects of centrally acting angiotensin II AT1 receptor antagonists. Regul Pept 128, 227-238 (2005).
20. Watanabe, T., Fujioka, T., Hashimoto, M. & Nakamura, S. Stress and brain angiotensin II receptors. Crit Rev Neurobiol 12, 305-317 (1998).
21. Grove, K. L., Cook, V. I. & Speth, R. C. Angiotensin II receptors in the ventral portion of the bed nucleus of the stria terminalis. Neuroendocrinology 53, 339-343 (1991).
22. Lenkei, Z., Palkovits, M., Corvol, P. & Llorens-Cortes, C. Expression of angiotensin type-1 (AT1) and type-2 (AT2) receptor mRNAs in the adult rat brain: a functional neuroanatomical review. Front Neuroendocrinol 18, 383-439 (1997).
23. Song, K., Allen, A. M., Paxinos, G. & Mendelsohn, F. A. Mapping of angiotensin II receptor subtype heterogeneity in rat brain. J Comp Neurol 316, 467-484 (1992).
24. Cam, G., Mochizuki, T. & Saper, C. B. Neural circuitry of stress-induced insomnia in rats. J Neurosci 28, 10167-10184 (2008).
25. Nofzinger, E A., et al. Functional neuroimaging evidence for hyperarousal in insomnia. Am J Psychiatry 161, 2126-2128 (2004).
26. Miura, S.-I., Fujino, M., Hanzawa, H., Kiya, Y., Imaizumi, S., Matsuo, Y., Tomita, s., Uehara, Y., Karnik, S, Yanagisawa, H., Koike, H., Komuro, I., and Saku, K. Molecular mechanism underlying inverse agonist of angiotensin II type 1 receptor. J. Biol. Chem. 281 (28), 19288-19295 (2006).
27. Imaizumi, S., Miura, S.-I., Yahiro, E., Uehara, Y., Komuro, I., and Saku, K. Class- and molecule-specific differential effects of angiotensin II type 1 receptor blockers. Curr. Pharm. Des. 2012, Nov. 21 (epub ahead of print; PMID:23176212).
28. Miura, S. and Saku, K. Do all angiotensin II type 1 receptor blockers have the same beneficial effects? Br. J. Pharmacol. 151,912-913 (2007).

Various references are cited herein, the contents of which are hereby incorporated by reference in their entireties.

We claim:

1. A method for treating primary insomnia in a subject in need thereof, comprising administering to the subject a therapeutically effective amount of an AT1 receptor blocker that promotes sleep, wherein the therapeutically effective amount is at least about 50% lower than a dosage of the AT1 receptor blocker for treating hypertension, wherein the AT1 receptor blocker is selected from the group consisting of azilsartan, candesartan, eprosartan, irbesartan, losartan, olmesartan, telmisartan, valsartan, and combinations thereof.

2. The method of claim 1, further comprising administering to the subject a second sleep-promoting agent.

3. The method of claim 2, wherein the second sleep-promoting agent is an H1 antagonist.

4. The method of claim 3, wherein the H1 antagonist is selected from the group consisting of diphenhydramine hydrochloride, doxepin, doxylamine succinate, orphenadrine, bromodiphenhydramine, and dimenhydrinate.

5. The method of claim 2, wherein the second sleep-promoting agent is selected from the group consisting of H3 agonists, immepip, imetit, methimepip, immethridine, R-alpha-methylhistamine, 4-benzyl-1H-imidazole-based H3 receptor agonists, and H3B agonists.

6. The method of claim 2, wherein the second sleep-promoting agent is a $GABA_A$ ligand with alpha-3 or alpha-2/alpha-3 agonist activity.

7. The method of claim 2, wherein the second sleep-promoting agent is selected from the group consisting of zolpidem, zaleplon, and eszopiclone.

8. The method of claim 2, wherein the second sleep-promoting agent is a benzodiazepine.

9. The method of claim 8, wherein the benzodiazepine is selected from the group consisting of diazepam, clonazepam, lorazepam, and alprazolam.

10. The method of claim 2, wherein the second sleep-promoting agent is a corticotropin releasing hormone antagonist.

11. The method of claim 1, further comprising administering to the subject a melatonin receptor agonist.

12. The method of claim 11, wherein the melatonin receptor agonist is selected from the group consisting of ramelteon, agomelatine, tasimelteon, TIK-301, and melatonin.

13. The method of claim 1, further comprising administering to the subject a homeopathic sleep aid.

14. The method of claim 13, wherein the homeopathic sleep aid is selected from the group consisting of tryptophan, L-tryptophan, lavender, chamomile, valerian root, passionflower, lemon balm, inositol, magnesium, humulus lupus, hops extract, St. John's wort, and melatonin.

15. The method of claim 11, wherein the melatonin receptor agonist is administered to the subject in a therapeutically effective amount that is lower than a dosage of the melatonin receptor agonist when the melatonin receptor agonist is the only sleep-promoting agent administered to the subject.

16. The method of claim 1, wherein the method promotes sleep in the subject through at least one of: decreasing sleep latency, increasing non-rapid eye movement (NREM) sleep, increasing rapid eye movement (REM) sleep, and not inducing atypical wave components in electroencephalogram (EEG).

* * * * *